United States Patent
Yancey et al.

(10) Patent No.: US 10,285,889 B2
(45) Date of Patent: May 14, 2019

(54) FEMORAL LIFT APPARATUS

(71) Applicants: Steele Yancey, Nashville, TN (US); Jeff Hodrick, Franklin, TN (US)

(72) Inventors: Steele Yancey, Nashville, TN (US); Jeff Hodrick, Franklin, TN (US)

(73) Assignee: Hy Innovation, LLC, Nashville, TN (US)

( * ) Notice: Subject to any disclaimer, the term of this patent is extended or adjusted under 35 U.S.C. 154(b) by 221 days.

(21) Appl. No.: 15/082,691

(22) Filed: Mar. 28, 2016

(65) Prior Publication Data

US 2017/0273846 A1    Sep. 28, 2017

Related U.S. Application Data

(60) Provisional application No. 62/169,228, filed on Jun. 1, 2015.

(51) Int. Cl.
*A61G 13/12* (2006.01)
*A61G 13/10* (2006.01)

(52) U.S. Cl.
CPC ....... *A61G 13/1245* (2013.01); *A61G 13/101* (2013.01)

(58) Field of Classification Search
CPC .......... A61G 13/101; A61G 2007/0519; A61G 13/1245; A61G 13/123; A61G 13/0081
See application file for complete search history.

(56) References Cited

U.S. PATENT DOCUMENTS

| | | | | |
|---|---|---|---|---|
| 4,901,964 A | * | 2/1990 | McConnell | A61G 13/101 24/514 |
| 5,329,934 A | * | 7/1994 | Bowman | A47D 13/08 128/870 |
| 5,933,887 A | * | 8/1999 | Strange | A61G 13/12 128/845 |
| 7,824,353 B2 | | 11/2010 | Matta | |

(Continued)

FOREIGN PATENT DOCUMENTS

EP    1931298 A2    6/2008

OTHER PUBLICATIONS

International Preliminary Report on Patentability for PCT/US2016/035245 (Year: 2017).*

(Continued)

*Primary Examiner* — Nicholas F Polito
*Assistant Examiner* — Amanda L Bailey
(74) *Attorney, Agent, or Firm* — Waller Lansden Dortch & Davis LLP; Blake M. Bernard

(57) ABSTRACT

A femoral lift apparatus for an operating table having a side rail, the apparatus engageable with the femur of a patient. The apparatus includes a lift mountable to the side rail. An extension arm is receivable on the lift, the extension arm extending transversely from the lift when the extension arm is received on the lift. A plurality of apertures can be defined along the extension arm, and a femoral hook can be receivable in one of the apertures in the extension arm, the femoral hook having a hook end shaped to be received under and contour the femur of the patient positioned on the operating table when the lift is mounted to the side rail of the table, the extension arm is received on the lift, and the femoral hook is received in one of the apertures of the extension arm.

16 Claims, 6 Drawing Sheets

(56) References Cited

U.S. PATENT DOCUMENTS

| | | | | |
|---|---|---|---|---|
| 8,683,631 B2* | 4/2014 | Bellows | ............. | A61G 13/0036 |
| | | | | 128/845 |
| 2007/0251011 A1* | 11/2007 | Matta | ................. | A61B 19/0248 |
| | | | | 5/624 |
| 2015/0094780 A1* | 4/2015 | Krickeberg | .......... | A61G 13/101 |
| | | | | 606/86 R |

OTHER PUBLICATIONS

Innomed Hip Instruments, 25 pages, http://www.innomed.net/hip_anterior_approach.htm; Dec. 21, 2014.
European Search Report dated Dec. 1, 2018, nine pages.

* cited by examiner

FEMORAL LIFT APPARATUS

CROSS-REFERENCES TO RELATED APPLICATIONS

This application is a non-provisional of U.S. Patent Application Ser. No. 62/169,228 filed Jun. 1, 2015 entitled Table Mounted Femoral Lift which is herein incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to surgical lift devices for an hip replacement surgery. Hip replacement surgery can be performed through a variety of approaches. Traditionally it has been performed either through a posterior approach, anterolateral approach, or direct lateral approach. These approaches have a shared disadvantage of disrupting muscular tissue surrounding the hip. More recently, the direct anterior approach to hip replacement has become popular. This approach allows the procedure to be performed without violating muscular tissue, but instead spreading the muscular tissue apart to access the hip joint. Procedure specific direct anterior operating room tables have been designed to facilitate the performance of hip replacement through this approach. These tables, while effective, come with some inherent disadvantages. They carry a relatively high cost compared to standard operating room tables. The operation of the table requires specialized operating room staff. The table has a large spatial footprint which requires additional storage space as well as larger operating rooms. The procedure can be performed without a specialized table, however this is often more difficult, especially in regards to femoral preparation.

What is needed then are improvements to hip surgery devices for an direct anterior approach procedure.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure is a femoral lift apparatus for a standard operating table having a side rail running along a lateral side of the table, the lift apparatus engageable with the femur of a patient. The apparatus can include a lift mountable to the side rail of the operating table. An extension arm can be receivable on the lift, the extension arm extending transverse from the lift when the extension arm is received on the lift. A plurality of apertures can be defined along the extension arm. A femoral hook can be receivable in one of the apertures in the extension arm, the femoral hook having a hook end shaped to be received under and contour the femur of the patient positioned on the operating table when the lift is mounted to the side rail of the table, the extension arm is received on the lift, and the femoral hook is received in one of the apertures.

Another aspect of the present disclosure is a femoral lift apparatus for a standard operating table having a side rail running along a lateral side of the table, the lift engageable with the femur of a patient, the apparatus including a lift mountable to the side rail of the operating table, the lift including a movable drive shaft, the drive shaft having a longitudinal axis oriented substantially vertically when the lift is mounted on the side rail of the operating table, the drive shaft having a distal end. An extension arm can be receivable on the distal end of the drive shaft, the extension arm extending transverse from the drive shaft at a downward angle when the lift is mounted on the side rail and the extension arm is received on the drive shaft. A plurality of apertures can be defined along the extension arm, each aperture having an aperture axis oriented substantially parallel to the longitudinal axis of the drive shaft when the extension arm is received on the drive shaft. A femoral hook can be receivable in one of the apertures in the extension arm, the femoral hook having a hook end shaped to be received under and contour the femur of the patient positioned on the operating table when the lift is mounted to the side rail of the table, the extension arm is received on the lift, and the femoral hook is received in one of the apertures.

Another aspect of the present disclosure is a femoral lift apparatus for an operating table having a side rail running along a lateral side of the table, the lift engageable with the femur of a patient, the apparatus including a powered lift. A first rail clamp and a second rail clamp can be connected to the lift, the first and second rail clamps selectively mounting the lift to the side rail. An extension arm can be receivable on the lift, the extension arm extending transverse from the lift when the extension arm is received on the drive shaft. A plurality of apertures can be defined along the extension arm. A femoral hook can be receivable in one of the apertures in the extension arm, the femoral hook having a hook end shaped to be received under and contour the femur of the patient positioned on the operating table when the lift is mounted to the side rail of the table, the extension arm is received on the lift, and the femoral hook is received in one of the apertures.

One objective of the present disclosure is to provide a femoral lifting device that can be mounted to the side rail of a standard operating table.

Another objective of the present disclosure is to provide a lifting device that can be used for lifting a femur of either a patient's right or left leg.

Another objective of the present disclosure is to provide a femoral lifting apparatus that helps reduce invasion into a surgeon's working space.

Another objective of the present disclosure is to lower equipment costs for certain types of surgical procedures, including hip replacement procedures.

Numerous other objects, advantages and features of the present disclosure will be readily apparent to those of skill in the art upon a review of the following drawings and description of a preferred embodiment.

DETAILED DESCRIPTION

Figure 1:
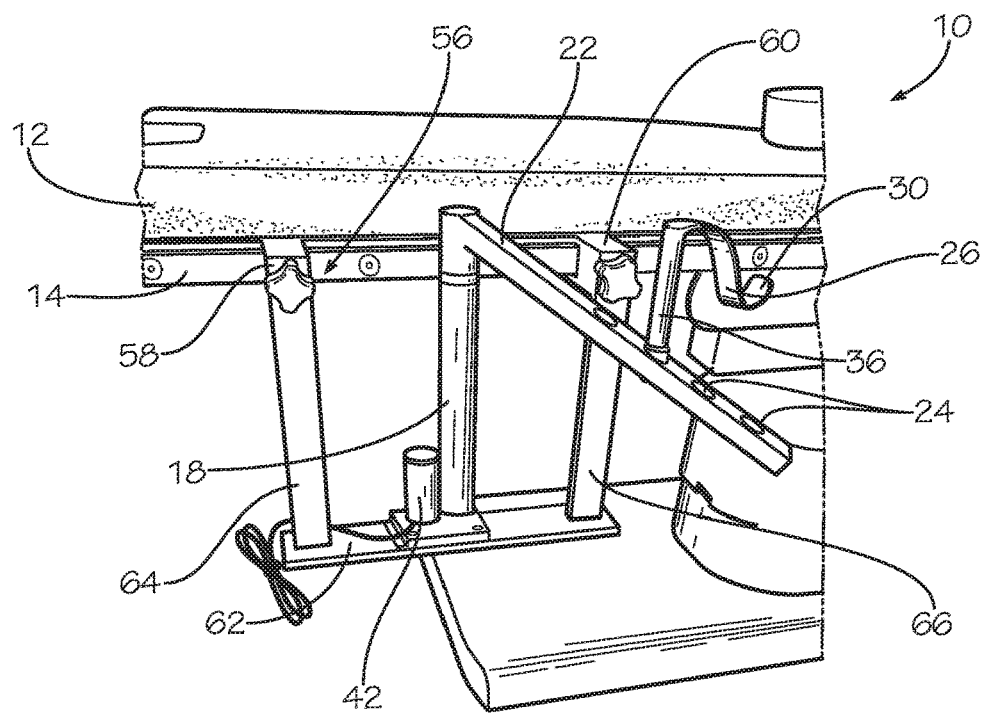
FIG. 1 is a perspective front view of a femoral lift apparatus engaged with a side rail of a standard operating table.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

Figure 2:
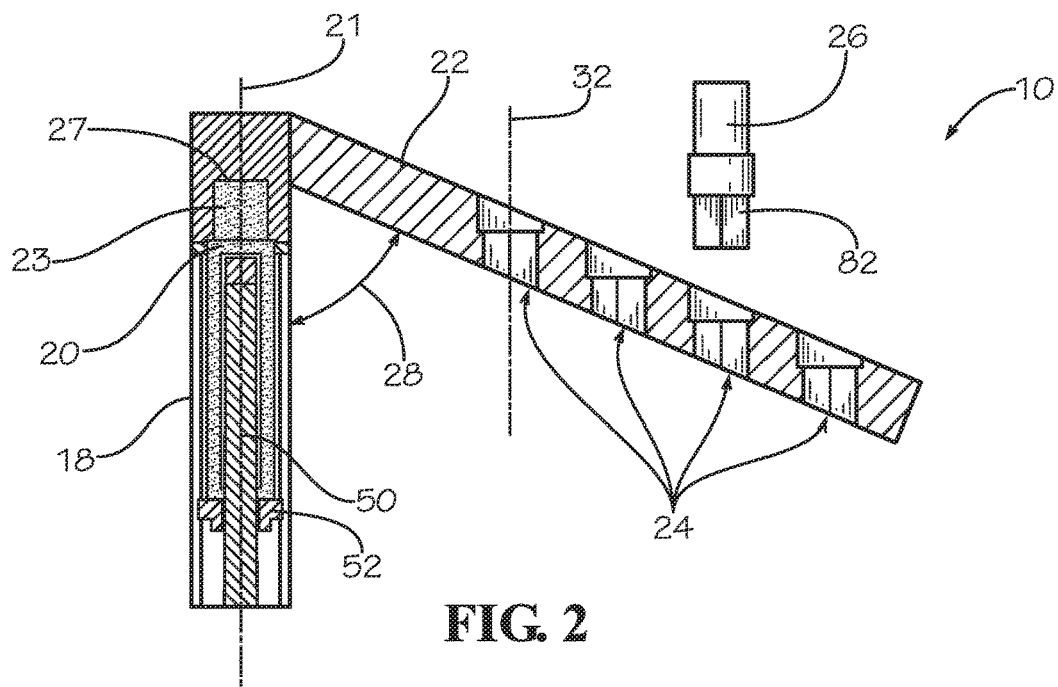
FIG. 2 is a partial cross section view of a lift, extension arm, and femoral hook of the apparatus of FIG. 1.

An embodiment of a femoral lift apparatus 10 of the present disclosure is shown in FIGS. 1-2. Apparatus 10 can be mountable to an operating table having at least one side rail 14 running along a lateral side 16 of operating table 12. Apparatus 10 can include a lift 18 mountable to side rail 16 of operating table 12. An extension arm 22 can be receivable on lift 18. Extension arm 22 can extend transversely from lift 18.

Extending transversely from lift 18 means that extension arm 22 is not oriented parallel with a longitudinal axis 21 of lift 18 when extension arm 22 is received on lift 18, and extension arm 22 generally forms a non-zero angle 28 with longitudinal axis 21. In some embodiments, extension arm 22 can extend perpendicularly from longitudinal axis 21. In other embodiments, as shown in FIG. 2, angle 28 can be less than ninety degrees such that when lift 18 is mounted on a side rail of an operating table and extension arm 22 is received on lift 18, extension arm 22 extends from drive shaft 20 at a downward angle. Having extension arm 22 extend at a downward angle from lift 18 can help reduce the intrusion of extension arm 22 into a surgeon's workspace during the procedure.

Extension arm 22 can include a plurality of apertures 24 defined through extension arm 22. Apparatus 10 can include a femoral hook 26 which can be receivable in one of the apertures 24. Femoral hook 26 can include a hook end 30 which can be shaped to be received under and contour the patient's femur during surgery when the lift is mounted to side rail 14 of operating table, extension arm 22 is received on lift 18, and femoral hook is received in extension member 22.

In some embodiments, lift 18 can include a movable drive shaft 20 which can be selectively extended in and out of lift 18. In some embodiments, longitudinal axis 21 of lift 18 can also be the longitudinal axis 21 of drive shaft 20. Drive shaft 20 can be movable on lift 18 along its longitudinal axis 21. Longitudinal axis 21 of lift 18 and driveshaft 20 can be oriented substantially vertically when lift 18 is mounted to a side rail of an operating table 12, such that drive shaft 20 can move vertically up and down on lift 18. Drive shaft 20 can have a distal end 23 extending from lift 18. In some embodiments, extension arm 22 can have a drive shaft socket 27 which can be shaped to receive distal end 23 of drive shaft 20. Extension arm 22 can extend transversely from drive shaft 20 when extension arm 22 is received on distal end 23 of drive shaft 20.

Figure 10:
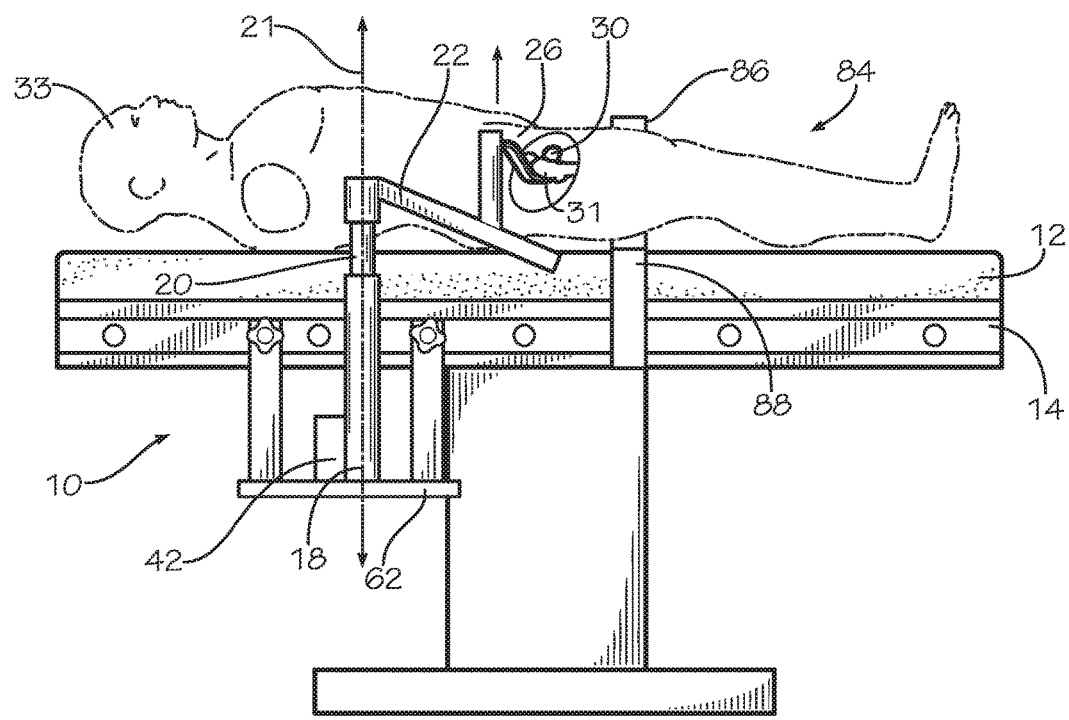
FIG. 10 is a front view of the apparatus of FIG. 1 engaging a patient's femur on the operating table.

As such, as shown in FIG. 10, during surgery, lift 18 can be mounted on side rail 14 of operating table 12 with the longitudinal axis 21 of lift 18 and drive shaft 20 oriented vertically. Extension arm 22 can be received on drive shaft 20 and femoral hook 26 can be received in one of the apertures on extension arm 22. Lift 18 and extension arm 22 can then be adjusted by the surgeon such that hook end 30 of femoral hook 26 can be positioned under the femur 31 of a patient 33. Lift 18 can be actuated to lift extension arm 22 and femoral hook 26 vertically upward, such that femur 31 can be loosened from the surrounding muscle in the patient's leg and lifted upward such that the surgeon can have access to femur 31 for the hip replacement procedure.

Apparatus 10 can have many benefits for a direct anterior approach hip replacement procedure over conventional direct anterior approach specific tables. Lifts on such conventional direct anterior approach specific tables are specially designed for those custom tables. Therefore, such conventional lifts are used only in conjunction with a large, expensive, and highly specialized operating table. In some situations, such a specialized operating table can be prohibitively costly for a medical center to purchase, such that the medical center makes the decision to not provide such a procedure for its patients. Apparatus 10 on the other hand can be attached to many standard operating tables which are currently being used by various medical facilities which include one or more side rails. As such, medical centers can have the option of purchasing just a femoral lift, which can be mounted on existing tables for such direct anterior approach hip replacement procedures, without having to purchase a highly specialized table. For surgeries that do not require a lift, apparatus 10 can simply be removed and stored. Being able to separately purchase a femoral lifting device that is readily adaptable to be mounted to a medical facility's existing operating tables can help lower the equipment costs associated with procedures that may benefit from such a lifting device, making such procedures more affordable for smaller medical facilities outside of the typical hospital environment, and thereby more available to patients.

Referring again to FIG. 2, in some embodiments, each of apertures 24 in extension arm 22 can have an aperture axis 32. In some embodiments, when lift 18 is mounted to the side rail of the operating table and extension arm 22 is received on lift 18 via distal end 23 of drive shaft 20, aperture axis 32 can be oriented substantially parallel with longitudinal axis 21 of drive shaft 20. As such, when apparatus 10 is in use, aperture axis 32 can be oriented substantially vertically. When femoral hook 26 is received in one of the apertures 24, femoral hook 26 can extend upward from apertures 24 in a substantially vertical direction.

Figure 3:
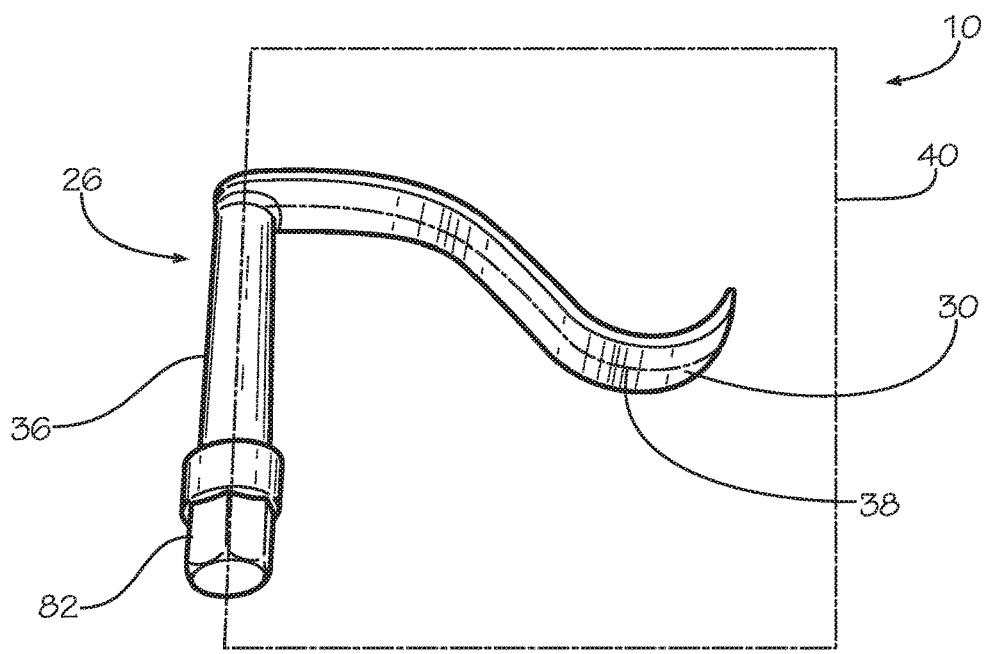
FIG. 3 is a side perspective view of a femoral hook of the apparatus of FIG. 1.
Figure 4:
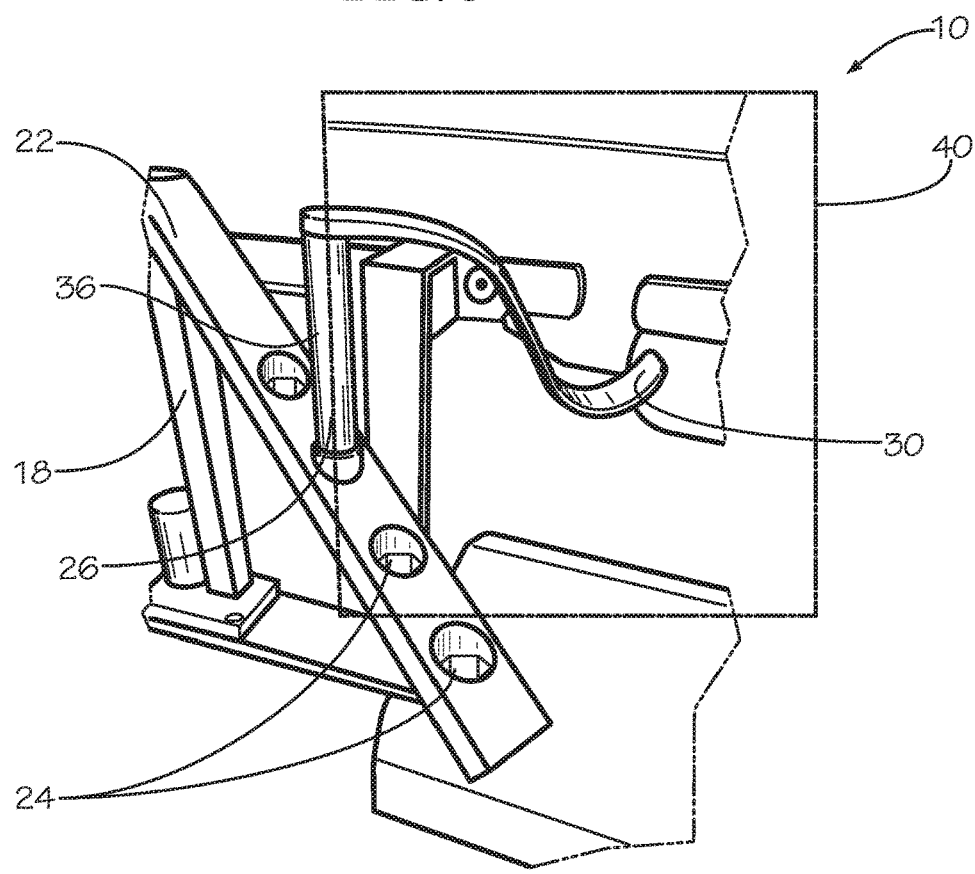
FIG. 4 is a detailed view of an extension arm and a femoral hook of the apparatus of FIG. 1.

Referring now to FIGS. 2-4, in such embodiments where the aperture axis 32 is oriented substantially vertically or substantially parallel to a longitudinal axis 21 od drive shaft 20 when the surgery lift apparatus 10 is in use, femoral hook 26 can be shaped such that lift 18 can be mounted to either side of the operating table and femoral hook can contour the corresponding left or right leg femur on that side of the operating table. Femoral hook 26 can include a hook shaft 36 and hook end 30, hook shaft 36 receivable in one of the apertures 24, hook end 30 extending from hook shaft 36. Hook end 30 in some embodiments can extend planarly from hook shaft 36. Extending planarly can mean that a midline 38 of hook end 30 can extend or curve along a single reference plane 40. In some embodiments, hook shaft 36 can be collinear with the reference plane 40 such that hook shaft 36 and hook end 30 both lie on a single reference plane 40. As such, in embodiments where aperture axes 32 are oriented substantially vertically or parallel with the longitudinal axis 21 of the drive shaft 20 when lift 18 is mounted to the side rail of the operating table and extension arm 22 is received on drive shaft 20, hook shaft 36 can be received in apertures 24 and extend substantially vertically from extension arm 22, and hook end 30 can extend from hook shaft 26 along a vertical reference plane 40.

Having an aperture axis 32 oriented vertically and a hook shaft 36 and hook end 30 oriented within a single plane can allow femoral hook 26 to be positioned in one of the apertures 24 of extension arm 22 and maintain the same general orientation no matter which side of the operating table apparatus 10 is mounted. As such, femoral hook 26 can be suitable for use on the femur of either a patient's right or left leg. Additionally, having femoral hook 26 contained within a single reference plane can help reduce the cost of manufacturing the femoral hook 26 as the hook 26 does not curve three dimensionally and as such can be easier to produce.

Figure 5:
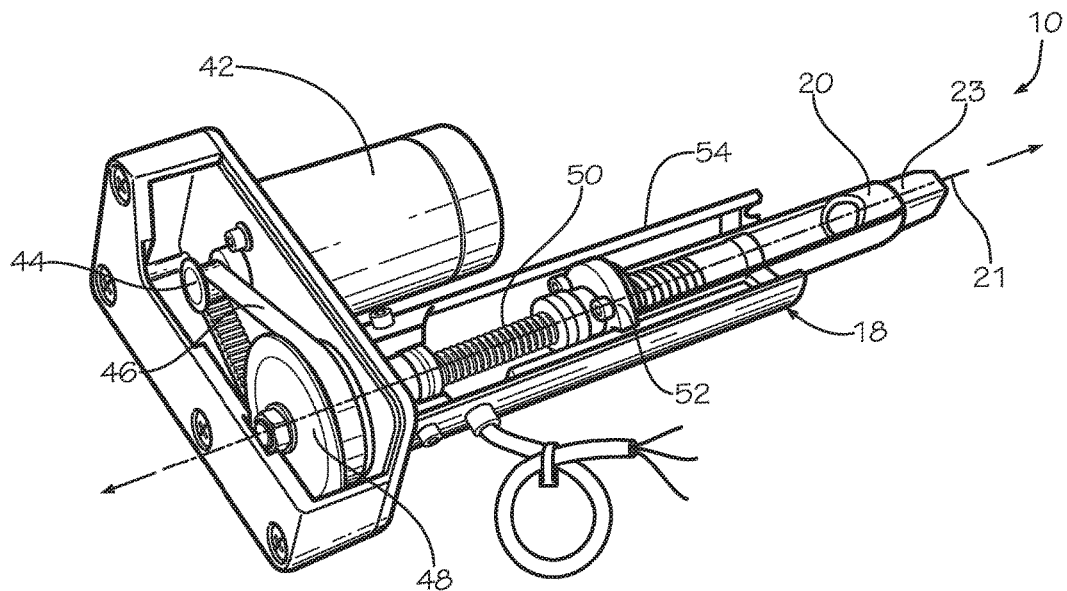
FIG. 5 is a detailed cutaway view of a lift of FIG. 1.

Lift 18 can be any suitable lifting device configured to produce vertical motion of extension arm 22 and femoral hook 26. A cutaway view of lift 18 of FIG. 1 is shown in FIG. 5. In some embodiments, lift 18 can be powered such that lift 18 can run automatically. In other embodiments, lift 18 can be a manually operated. In some embodiments, lift 18 can be a linear actuator which can move drive shaft 20 linearly along its longitudinal axis 21. In some embodiments, lift 18 can include a linear stage which can be moved linearly by lift 18, drive shaft 20 extending from the linear stage.

In one embodiment, lift 18 is a motorized linear actuator. Lift can include motor 42. Motor 42 can turn motor shaft 44. Motor shaft 44 can engage a drive belt 46. Drive belt 46 can be disposed around a pulley 48. As motor 42 turns motor shaft 44 to turn drive belt 46, drive belt 46 can in turn rotate pulley 48. Pulley 48 can be coupled to a threaded lift screw 50 which can turn as pulley 48 is rotated by drive belt 46. An angular stop block 52 can be disposed around threaded lift screw 50, angular stop block 52 having internal threads that can mesh with the threads on threaded lift screw 50. Lift 18 can have an outer cover 54 having one or more lateral side channels defined therein. Angular stop block 52 can have one or protrusions extending into the one or more channels such that the channels prevent angular stop block 52 from turning with lift screw 50. Because angular stop block 52 is prevented from turning with lift screw 50, angular stop block 52 translates along lift screw 50 as lift screw turns. Drive shaft 20 can be connected to angular stop block 52 such that drive shaft 20 translates along lift screw 50 with angular stop block 52. As such, as lift screw 50 turns, distal end 23 of drive shaft 20 is translated linearly in and out of outer cover 54 of lift 18, depending on the direction in which lift screw 50 turns.

In some embodiments, motor 42 can be an AC or DC electric motor. In some embodiments, pulley 48 and drive belt 46 system can be replaced by coupling meshing gears to motor shaft 44 and lift screw 50. In some embodiments, intermediate gears can be used to engineer a gear ratio between motor shaft 44 and lift screw 50 such that the speed of the linear motion of drive shaft 20 can be controlled. Lift 18 can also include one or more limit switches which effectively limit or stop linear movement of angular stop block 52 and drive shaft 20 in either direction along longitudinal axis 21. In still other embodiments, lift 18 can be a hydraulic or pneumatic lift, including a hydraulic or pneumatic linear actuator.

Referring again to FIG. 1, in some embodiments, apparatus 10 can include a clamp system 56 connected to lift 18. In some embodiments, clamp system 56 can include a first rail clamp 58 and a second rail clamp 60. First rail clamp 58 can be positioned on a first lateral side of lift 18, and second rail clamp 60 can be positioned on a second lateral side of lift 18. As such, first and second rail clamps 58 and 60 can provide balanced attachment of lift 18 to side rail 14, rail clamps 58 and 60 supporting both lateral sides of lift 18. Such a balanced support of lift 18 can help prevent lift 18 from leaning laterally one way or another during operation of apparatus 10. In other embodiments, clamp system 56 can include a single clamp selectively mounting lift 18 to side rail 14.

In some embodiments, apparatus 10 can include a lift platform 62. Lift 18 can be mounted on lift platform 62, and lift 18 can be mountable to side rail 14 of operating table 12 via lift platform 62. In such embodiments, clamp system 56 can be connected to lift 18 via lift platform 20. First rail clamp 58 can include a first clamp arm 64 connected to lift platform 62 on a first lateral side of lift 18, and second rail clamp 60 can include a second rail clamp arm 66 connected to lift platform 62 on a second lateral side of lift 18. As such, first and second rail clamps 58 and 60 can be connected to lift 18 via lift platform 62.

As can be seen from FIG. 1, first rail arm 64 and second rail arm 66 can extend downward from side rail 14 when lift 18 is mounted to side rail 14, such that lift platform 62 can be positioned below side rail 14. As such, the majority of lift 18 and lift platform 62 can generally be positioned below side rail 14 and the patient during surgery such that lift 18 is generally out of the working area of the surgeon. Extension arm 22 extending laterally or transverse from drive shaft 20 of lift 18 can also help locate lift 18 laterally from the hip of the patient during surgery such that lift 18 is both laterally away from and below the surgeon's working area. This can be a benefit over some conventional femoral lift devices which can extend upward from side rail 14 and can be positioned over the patient and directly within the surgeon's work space during the procedure.

Figure 6:
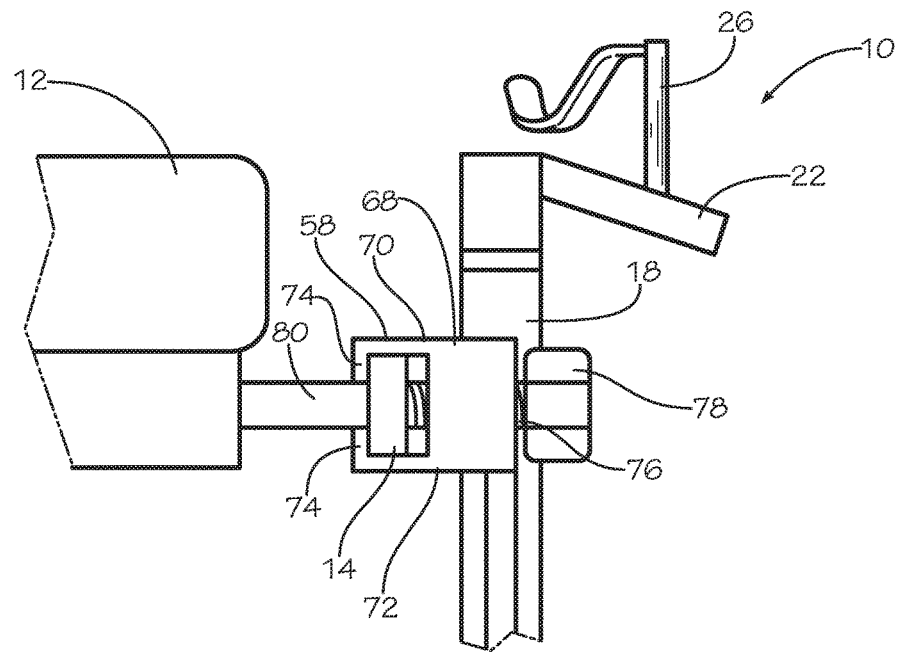
FIG. 6 is a partial side view of the apparatus of FIG. 1, showing the connection of a clamp system to a side rail of an operating table.

Referring now to FIG. 6, in some embodiments, each rail clamp 58 in clamp system 56 can include a clamp bracket 68 which can slide over side rail 14. Clamp bracket 68 can include a top wall 70 and bottom wall 72 which can slide over top and bottom edges of side rail 14, and a retention member 74 extending inward from each of top and bottom walls 70 and 72 of clamp bracket 68. Clamp bracket 68 can also include a clamp screw 76 with a knob 78 that can extend through clamp bracket 68 and selectively engage side rail 14. When clamp bracket 68 is received on side rail 14, clamp screw 76 can be screwed into clamp bracket 68 via knob 78. As clamp screw 76 is tightened, retention members 74 are biased to engage an inner side of side rail 14 while clamp screw 76 engages an outer side of side rail 14, which effectively clamps clamp bracket 68, and thereby lift 18, to side rail 14.

In some embodiments, side rails 14 are connected to operating table 12 via rail post 80. Retention members 74 can be spaced apart such that a gap is formed between retention members 74. When clamp bracket 68 is slid onto side rail 14, retention members 74 can slide over or around rail posts 80 while still being able to engage the inner side of side rail 14 when clamp screw is tightened. As such, in some embodiments, the position of apparatus 10 and lift 18 can be adjustable along the entire length of side rail 14. Having retention members 74 extending from both the top and bottom of clamp bracket 68 can also help secure clamp 58 to side rail 14 at both the top and bottom of clamp bracket 68, which can help prevent forward and backward rotation or movement of lift 18 when lift 18 is mounted on side rail 14, while having first and second rail clamps 58 and 60 positioned on either side of lift 18 can help prevent lateral rotation or movement when lift 18 is mounted to side rail 14. Preventing forward, backward, and lateral motion and rotation can help maintain drive shaft 20, and thus the direction of lifting, in a vertical orientation during the surgical procedure.

Figure 7:
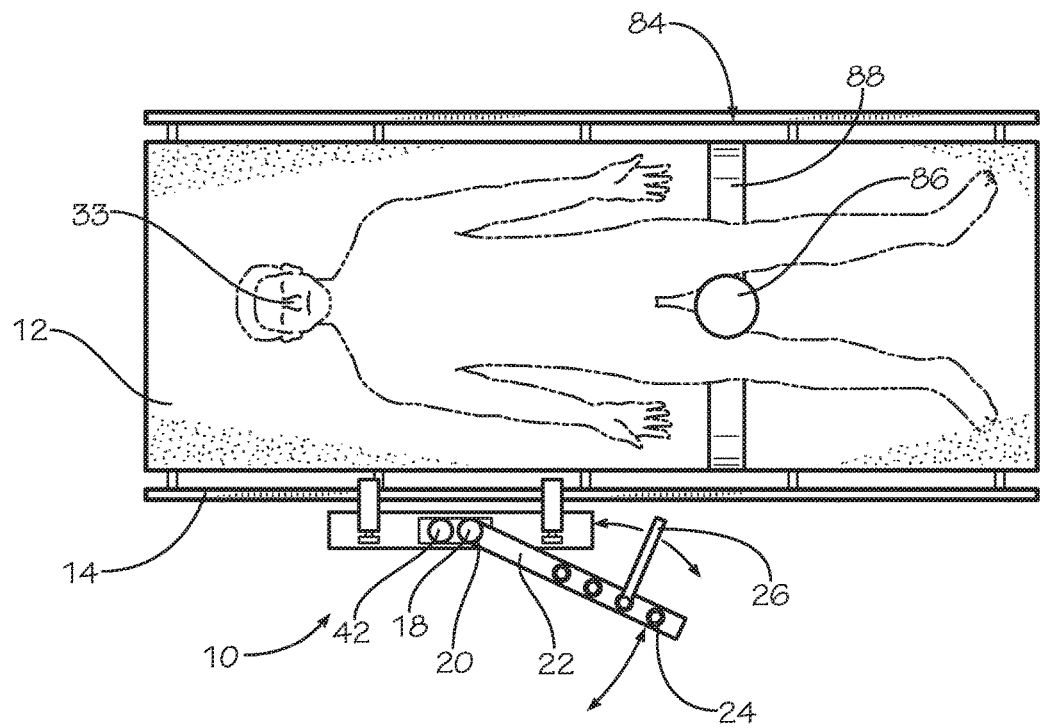
FIG. 7 is a top view of an operating table showing the apparatus of FIG. 1 and a detachable hip locator connected to the operating table.

Referring now to FIG. 2, in some embodiments, extension arm 22 can be rotatably disposed on lift 18. In some embodiments, distal end 23 of drive shaft 20 can have a generally round or circular shape, and drive shaft socket 27 can include a corresponding round or circular shape such that drive shaft socket 27 and extension arm can rotate about distal end 23 of drive shaft 20. As such, extension arm 22 can be rotated to move femoral hook 26 received on extension arm 22 towards or away from operating table 12 and a patient on the operating table, as shown in FIG. 7. Such an inward and outward movement of femoral hook 26 can help facilitate use of apparatus 10 on patients of various sizes.

Figure 8:
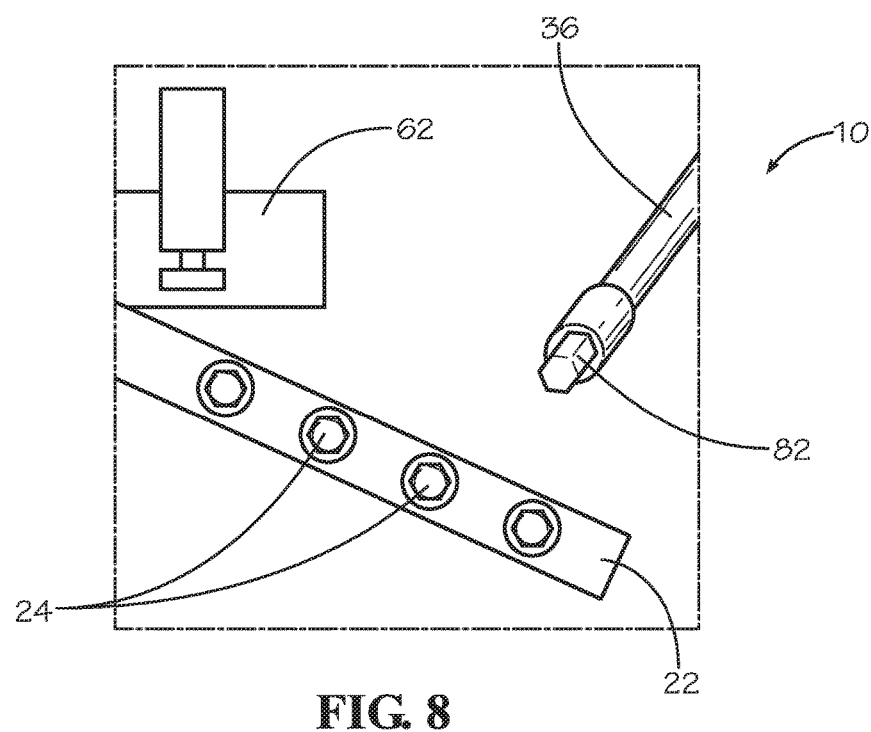
FIG. 8 is a detailed view of the apparatus of FIG. 7 showing the insertion of the femoral hook into an aperture of an extension arm.

Additionally, as shown in FIG. 8, in some embodiments femoral hook 26 can have an attachment end 82 on hook shaft 36. Attachment end 82 can be shaped to allow femoral hook 26 to selectively be received in one of apertures 24 at discrete angular positions with respect to extension arm 22. For instance, in some embodiments, attachment end 82 of femoral hook 26 can have a hexagonal shape. At least a portion of each aperture 24 can have a corresponding hexagonal shape. As such, femoral hook 26 can be received in apertures 24 at discrete angles which can be chosen by the surgeon as desirable. However, once femoral hook 26 is received in aperture 24, the corresponding hexagonal shapes of attachment end 82 and the portion of aperture 24 can prevent femoral hook 26 from rotating with respect to extension arm 22. In other embodiments, attachment end 82 and apertures 24 can have a variety of suitable corresponding shapes to product discrete angular positions of femoral hook 26 in apertures 24, including but not limited to, triangular, square, pentagonal, heptagonal, octagonal, cross shaped, star shaped, etc.

As femoral hook 26 is moved towards and away from operating table 12 as extension arm 22 rotates about drive shaft 20, the orientation of femoral hook 26 with respect to operating table 12 can change. It may be desirable as extension arm 22 rotates to place femoral hook 26 at another discrete angular position within aperture 24 to maintain an optimum alignment or orientation of femoral hook 26 with operating table 12 and a femur of the patient positioned on operating table 12. Having both extension arm 22 being rotatable with respect to drive shaft 20 and femoral hook 26 positionable at discrete angular positions with respect to extension arm 22 can allow apparatus 10 to be used on patients of varying sizes while still helping maintain an optimal alignment or orientation of femoral hook 26 with a patient's femur on which the surgeon is operating.

In some embodiments, apparatus 10 can further include a hip locator attachment 84 which is securable to operating table 12, shown in FIGS. 7 and 10. Hip locator attachment 84 can include a hip locator column 86 and one or more straps 88 extending from hip locator column 84. Straps 88 can selectively secure hip locator column 86 to operating table such that hip locator column 86 can be in a spaced relation with femoral hook 26. Hip locator column when secured to operating table 12 by straps 88 can extend upwardly from the operating table to provide a post or location point to desirably position patient 33 on operating table 12. With lift 18 mounted to side rail 14, hip locator attachment 84 can be secured and positioned on operating table 12 such that when a patient lies on a table with hip locator column between the patient's legs and against the patient's pelvis, femoral hook 26 can be oriented to be selectively positionable over the hip joint of patient 33 as extension arm 22 rotates about drive shaft 20. Hip locator attachment 84 can also be useful during the hip replacement surgery to provide a resistance force while locating and dislocating the hip replacement.

Straps 88 can include any suitable mechanism for securing hip locator column 86 on operating table 12. In some embodiments, straps 88 can include one or more fasteners for securing straps 88 together around the operating table, or for securing straps 88 to respective side rails 14 of operating table 12. For instance, some straps 88 can include snaps, clips, buttons, clasps, hook and loop fasteners, hooks, etc. for securing straps 88 together or to side rails 14. In some embodiments, straps 88 may also include a manual or automatic winch or other suitable tightening device. Straps 88 can be loosely connected to each other around operating table 12 or to side rails 14 and the winch can be used to remove the slack from straps 88 and tightly secure hip locator column 86 to operating table 12.

Figure 9:
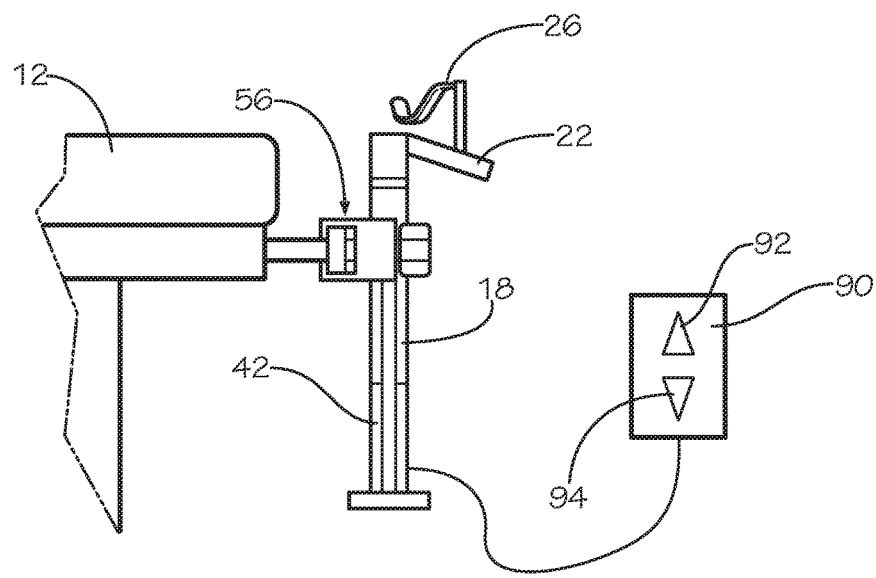
FIG. 9 is a side view of the apparatus of FIG. 1 further including a remote actuator for the lift.

Referring now to FIG. 9, in some embodiments, apparatus 10 can include a remote actuator 90 communicated with lift 18. Remote actuator 90 can include an up button 92 or down button 94 which can be selectively depressed by the surgeon to control the height of lift 18 and femoral hook 26. In other embodiments, remote actuator 90 can include a switch which can be selectively alternated between an up, down, and neutral position. Remote actuator 90 is shown in FIG. 9 as a hand held remote. In other embodiments, remote actuator 90 can be a foot pedal that can be placed on the floor and actuated by a surgeon's foot such that the surgeon does not have to free a hand during the procedure in order to adjust lift 18.

In some embodiments, remote actuator 90 can be electrically communicated with lift 18 via one or more wires. In other embodiments, remote actuator 90 can be configured to communicate with lift 18 via wireless telemetry or radio frequency (RF) technology. In some embodiments, remote actuator 90 can include a radio frequency transmitter and lift 18 can include a receiver, the transmitter sending a signal from remote actuator 90 to the receiver on lift 18 in response to a surgeon actuating one of the buttons or switches on the remote actuator 90.

Figure 11:
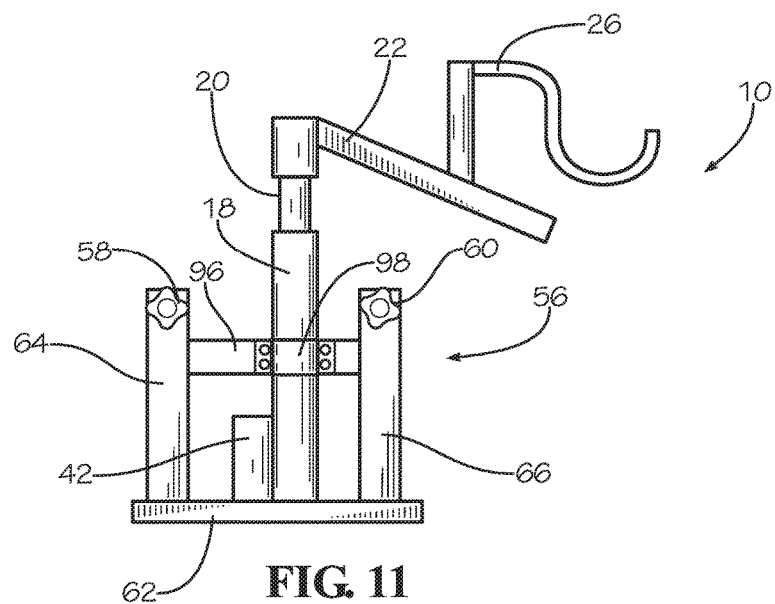
FIG. 11 is a front view of another embodiment of a femoral lift apparatus having a lift mounted to both a lift platform and a support bar extending between first and second clamp rails.

Referring now to FIG. 11, in some embodiments, apparatus 10 can further include a support brace 96 connected to and extending between the first clamp arm 64 and second clamp arm 66. Lift 18 can be mounted to both lift platform 62 and support brace 92. Lift 18 can be mounted to support brace via a suitable mounting bracket 98 which can be bolted or screwed to support brace 96. While lift 18 can be securely mounted to lift platform and supported on either lateral side by first and second rail clamps 58 and 60 when lift 18 is mounted on the side rail of an operating table, as the lift engages the femur and faces resistance, the resistance can put lift 18 under stress which can potentially cause lift to bend or twist on lift platform 18. Having lift 18 also mounted to support brace 96 can help provide structural support to lift 18, as well as to clamping system 56 during the procedure when femoral hook 26 engages and lifts the femur of a patient via lift 18.

Figures 12, 12A:
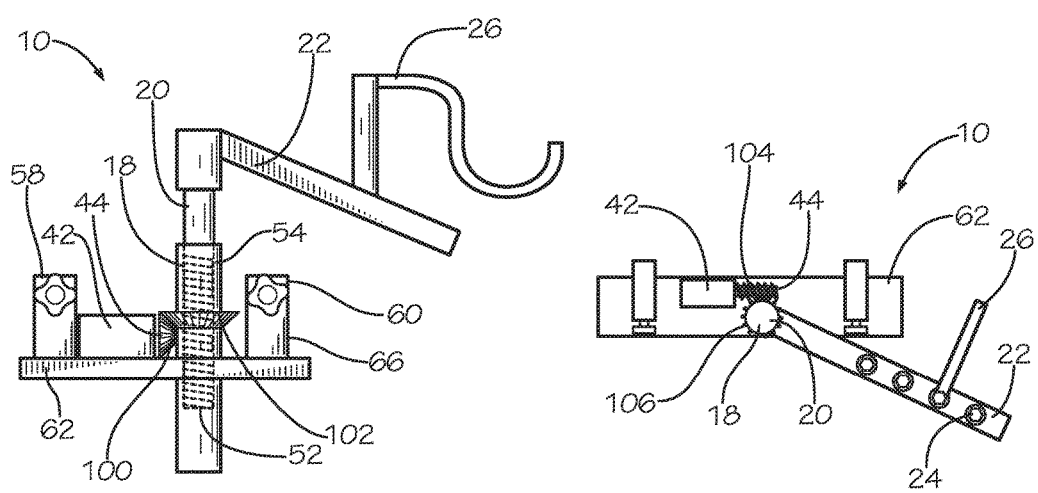
FIG. 12 is a front view of still another embodiment of a femoral lift apparatus having a portion of a lift extending below a lift platform.
FIG. 12A is a top view of another embodiment of a femoral lifting device showing a motor driving a worm gear that engages a corresponding gear on a lift.

In some embodiments, as shown in FIG. 1, a lower portion of lift 18 and motor 42 can be mounted on lift platform 62 such that all of lift 18 and motor extends upward from lift platform 62. In other embodiments, as shown in FIGS. 12 and 12A, at least a portion of lift 18 can extend below lift platform 62. In FIG. 12, motor 42 can be placed on its side and be equipped with an angled gear 100 on motor shaft 44. Lift 18 can be equipped with a corresponding angled gear 102 that is rotationally disposed on lift 18 generally near a middle portion of outer cover 54. A lower portion of lift 18 positioned below corresponding gear 102 can extend through a hole or aperture in lift platform 62 such that a portion of lift 18 extends below lift platform 62. Corresponding angled gear 102 can include internal threads that can engage screw 50 of lift 18. Angular stop block 52 can be connected to a lift screw 50 in such an embodiment, and drive shaft 20 can be integrally formed with lift screw 50. As such, as motor 42 turns the angled gears 100 and 102, angular stop block 52 can prevent lift screw 50 and drive shaft 20 from rotating such that lift screw 50 and drive shaft 20 are linearly translated with respect to angled gear 102 to extend in and out of lift 18 and lift femoral hook 26.

In some embodiments, lift 18 and motor 42 seen in FIG. 5 could also be modified such that pulley 48 was disposed generally in the middle of outer cover 54, with pulley 48 having internal threads that engage lift screw 50, with lift screw 50 and an integrated drive shaft 20 translating linearly with respect to pulley 48 as motor turns pulley 48. As such, motor 42 could remain in the same orientation as shown in FIG. 5 and drive belt 46 could turn pulley 48 as motor 44 rotates, while a portion of lift 18 extending below pulley 48 could extend through and below lift platform 62 shown in FIG. 1 when apparatus 10 was mounted on side rail 14 of operating table 12. As described previously, the pulley and drive belt system could also be replaced with meshing gears disposed on motor shaft 44 and lift 18 to produce the linear motion of drive shaft 20.

Referring now to FIG. 12A, in some embodiments, motor shaft 44 can be equipped with a worm gear 104 which can in turn can rotate a conventional gear 106 disposed generally in the middle portion of lift 18 as motor 44 rotates. Conventional gear 106 can be engaged with a lift screw of lift 18 similarly to the angled gear 102 of FIG. 12 such that as worm gear 104 turns conventional gear 106, the lift screw and drive shaft will be translated linearly to lift extension arm 22 and femoral hook 26, when extension arm 22 is received on the drive shaft and femoral hook 26 is received in extension arm 22.

In embodiments such as those shown in FIGS. 12 and 12A where a portion of lift 18 extends below lift platform 20, the overall profile and footprint of apparatus 10 can be reduced as apparatus 10 consumes less overall space near the operating table as lift platform 62 does not have to be positioned as far below the side rail as shown in FIG. 1. Instead, the lift platform 62 and motor 42 can be positioned relatively close to yet still beneath side rail 14. As such, the length of first and second rail clamp arms 64 and 66 can be decreased, thereby helping to decrease manufacturing costs of apparatus 10. Having the components of apparatus 10 closer to the side rail and further off of the ground can also help reduce the risk of those near the operating table inadvertently kicking and damaging the components of apparatus 10 when apparatus 10 is mounted on the side rail of the operating table.

Thus, although there have been described particular embodiments of the present invention of a new and useful SURGERY LIFT APPARATUS, it is not intended that such references be construed as limitations upon the scope of this invention.

What is claimed is:

1. A femoral lift apparatus for an operating table having a side rail running along a lateral side of the table, the lift apparatus engageable with the femur of a patient, the apparatus comprising:
    a lift mountable to the side rail of the operating table;
    an extension arm receivable on the lift, the extension arm extending transversely from the lift when the extension arm is received on the lift;
    a plurality of apertures defined along the extension arm; and
    a femoral hook having a hook shaft receivable in one of the apertures in the extension arm, each of the apertures in the extension arm having an aperture axis that is parallel to a longitudinal extension axis of the hook shaft when the hook shaft is received in the aperture, the femoral hook having a hook end shaped to be received under and contour the femur of the patient positioned on the operating table,
    wherein when the lift is mounted to the side rail of the table, the extension arm is received on the lift, and the femoral hook is received in one of the apertures of the extension arm, the extension arm extends in a downward direction from the lift, and the aperture axis is oriented in a vertical orientation.

2. The apparatus of claim 1, wherein
    the lift further comprises a movable drive shaft, the drive shaft having a longitudinal axis oriented substantially vertically when the lift is mounted on the side rail of the operating table;
    the drive shaft having a distal end; and the extension arm is receivable on the distal end of the drive shaft.

3. The apparatus of claim 1, wherein the extension arm is rotatably receivable on the lift.

4. The apparatus of claim 1, further comprising a clamping system connected to the lift, the clamping system selectively mounting the lift to the side rail of the operating table.

5. The apparatus of claim 4, wherein the clamping system further comprises a first rail clamp positioned in a first lateral side of the lift and a second rail clamp positioned on a second lateral side of the lift.

6. The apparatus of claim 5, further comprising a lift platform, the lift mounted to the lift platform, the first rail clamp and the second rail clamp connected to the lift via the lift platform.

7. The apparatus of claim 6, wherein the first rail clamp includes a first clamp arm, and the second rail clamp includes a second clamp arm, the first and second rail clamp arms connected to the lift platform such that the lift platform is positioned below the side rail of the operating table when the lift is mounted on the side rail.

8. The apparatus of claim 7, further comprising a support brace extending between the first clamp arm and the second clamp arm, the lift mounted to both the lift platform and the support brace.

9. The apparatus of claim 1, wherein the lift is powered.

10. The apparatus of claim 1, wherein the lift is a linear actuator.

11. The apparatus of claim 1, wherein:
at least a portion of each aperture in the extension arm has a hexagonal shape;
the hook end extends from the hook shaft, the hook shaft having an attachment end receivable in one of the apertures; and
the attachment end has a corresponding hexagonal shape.

12. The apparatus of claim 1, wherein the hook end extending from the hook shaft along a reference plane, the hook shaft being collinear with the reference plane.

13. The apparatus of claim 1, further comprising a remote actuator communicated with the lift.

14. The apparatus of claim 1, further comprising a lift platform, the lift mounted on the lift platform, the lift mountable to the side rail of the operating table via the lift platform, wherein at least a portion of the lift extends below the lift platform when the lift platform is mounted to the side rail.

15. A femoral lift apparatus for an operating table having a side rail running along a lateral side of the table, the lift apparatus engageable with the femur of a patient, the apparatus comprising:
a lift mountable to the side rail of the operating table, the lift including a movable drive shaft, the drive shaft having a longitudinal axis oriented substantially vertically when the lift is mounted on the side rail of the operating table, the drive shaft having a distal end;
an extension arm receivable on the distal end of the drive shaft, the extension arm extending transverse from the drive shaft at a downward angle when the lift is mounted on the side rail and the extension arm is received on the drive shaft;
a plurality of apertures defined along the extension arm, each aperture having an aperture axis oriented substantially parallel to the longitudinal axis of the drive shaft when the extension arm is received on the drive shaft; and
a femoral hook having a hook shaft receivable in one of the apertures in the extension arm, the aperture axis of each aperture oriented parallel to a longitudinal extension axis of the hook shaft when the hook shaft is received in the aperture, the femoral hook having a hook end extending from the hook shaft, the hook end shaped to be received under and contour the femur of the patient positioned on the operating table when the lift is mounted to the side rail of the table, the extension arm is received on the lift, and the femoral hook is received in one of the apertures of the extension arm.

16. The apparatus of claim 15, wherein the hook end extends from the hook shaft along a vertical reference plane when the lift is mounted to the side rail, the extension arm is received on the distal end of the shaft, and the femoral hook is received in one of the apertures on the extension arm, the hook shaft being collinear with the vertical reference plane.

* * * * *